United States Patent [19]

Scalesciani

[11] 4,327,105
[45] Apr. 27, 1982

[54] AMINO-PENICILLIN DERIVATIVE, AND THERAPEUTIC COMPOSITION CONTAINING THE SAME

[76] Inventor: Juan B. A. Scalesciani, Calle Y.B. Alberdi, Buenos Aires, Argentina

[21] Appl. No.: 241,641

[22] Filed: Mar. 9, 1981

[30] Foreign Application Priority Data

Dec. 2, 1980 [IT] Italy .................. 26351 A/80

[51] Int. Cl.³ .................. A61K 31/43; C07D 499/70
[52] U.S. Cl. .................. 424/271; 260/239.1
[58] Field of Search .................. 260/239.1; 424/271

[56] References Cited

U.S. PATENT DOCUMENTS

| | | | |
|---|---|---|---|
| 3,647,781 | 3/1972 | Wieslogle et al. | 260/239.1 |
| 3,767,646 | 10/1973 | Holdrege | 260/239.1 |
| 3,886,140 | 5/1975 | Lee | 260/239.1 |
| 3,959,258 | 5/1976 | Konig et al. | 260/239.1 |

Primary Examiner—Natalie Trousof
Assistant Examiner—Vera C. Clarke
Attorney, Agent, or Firm—Stevens, Davis, Miller & Mosher

[57] ABSTRACT

A new wide spectrum antibiotic of the penicillin class, of formula:

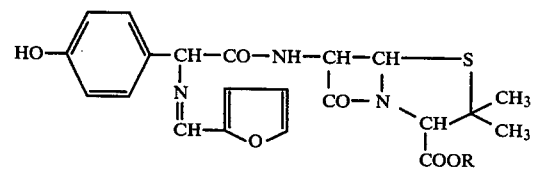

in which R=H, Na or K.

2 Claims, No Drawings

AMINO-PENICILLIN DERIVATIVE, AND THERAPEUTIC COMPOSITION CONTAINING THE SAME

This invention relates to a new derivative of the penicillin class possessing strong antibiotic activity, and to the process for its preparation and therapeutic compounds which contain it as their active principle.

The new compound according to the present invention is furfurylene-amino-p.hydroxybenzyl-penicillin of formula:

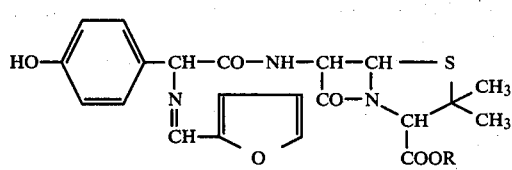

in which R=H, Na or K.

The process for preparing compound (I) consists essentially of reacting p.hydroxy-benzyl-aminopenicillin (Amoxycillin) with furfural according to the equation

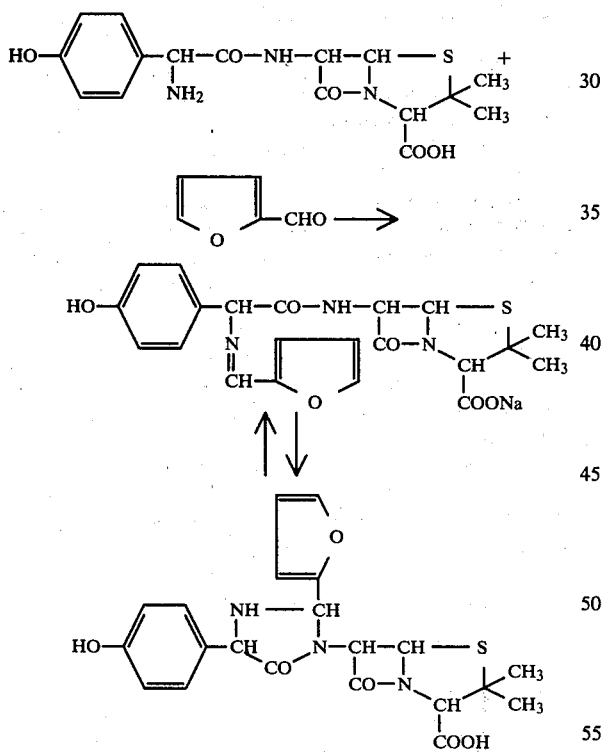

As can be seen from the aforesaid reaction scheme, the new penicillin, which for simplicity will be indicated by the symbol FU-2, is present in the reaction mixture in two isomer forms in equilibrium with each other. However, when isolated and dried, the compound FU-2 behaves uniformly as the product of formula (I), because of which hereinafter it will be considered exclusively as the product of formula (I).

Although the reaction on which the process according to the invention is based is a known reaction for preparing Schiff amine bases, in this specific case the realisation of the process has given rise to considerable difficulties in that the condensation reaction between the ammonium derivative and aldehyde derivative takes place in an alkaline solution, however when in alkaline solution penicillins become altered by hydrolysis, with resultant scission of the molecule.

It has however been found that there exists a narrow range of critical conditions within which the reaction can be carried out with high yields, and the product separated with pharmaceutical purity.

The conditions under which the process according to the present invention are carried out are: temperature 0°–10° C., aqueous solution of pH 6–7.2, reaction time 15–60 minutes.

The starting material used is an aqueous solution or suspension of Amoxycillin, obtained in any manner, and maintained at a temperature of 0°–10°.

The solution is adjusted to pH 6–7.2 with a Na or K hydrate, carbonate, or bicarbonate, furfural is added either as such or in the form of an aqueous solution, either in stoichiometric ratio or up to 50% excess, and the mixture is kept stirring for 15–60 minutes.

After this time, the solution is filtered, and the filtered mass is dried by lyophilising. The dry powder obtained is the sodium or potassium salt of the compound I.

A detailed description is given hereinafter in a non-limiting example, in order to facilitate the preparation of the new product according to the invention.

EXAMPLE 419 grams of Amoxycillin trihydrate are dissolved in 2 liters of cold water, the solution is cooled to 2°–3° C., and 96 g of furfural and 84 g of sodium bicarbonate are added under stirring.

Stirring is continued for 20 minutes, the mixture is then filtered trough a sterilising filter, and the separated product is lyophilised. The prepared product has a M.P. of 110°–112° C. (dec.), and a M.W. of 443. Elementary analysys gave the following empirical formula:

$C_{21}H_{21}O_6N_3S$.

The product gives the characteristic reactions of the β-lactam ring of the penicillins, and also the characteristic reactions of the furfural group.

The new compound (I) according to the present invention has proved to have a greater stability and greater antibacterial activity than the more known penicillins, and in particular than Amoxycillin.

The results of some significant tests are given hereinafter in order to demonstrate the usefulness of the new compound according to the invention in comparison with analogous known compounds.

1. Stability

The stability of the compound FU-2 with time and temperature was determined up to 90 days and up to 60° C. The results obtained are given in Table 1 below:

TABLE 1

|  | Amb. temp. | 40° C. | 50° C. | 60° C. |
| --- | --- | --- | --- | --- |
| Initial value | 100% | 90% | 90% | 90% |
| after 30 days | 89% | 88.4% | 80.1% | 79.7% |
| after 60 days | 88.6% | 88% | 80% | 78% |
| after 90 days | 88.1% | 88.1% | 79.6% | 78% |

In addition when preserved in an environment saturated with moisture, the compound has proved to be completely non-hygroscopic, in that the moisture content remained constantly at 40%.

The aforesaid values demonstrate that the new compound is considerably more stable than known penicillins.

2. Plasmatic Levels

A—Intravenous Injection

Three dogs were used having an average weight of 8-9 kg. The tests were carried out as a comparison between FU-2 and Amoxycillin, by injecting the drugs intravenously in a continuous manner at the rate of 5 ml/h of solution for a total time of 3 hours.

A total of 60.6 mg of Amoxycillin and 70 mg of FU-2 were injected, i.e. equimolecular quantities of the two compounds.

The tritation of the antibiotics was carried out by the bacteriological disc diffusion method using the method using the germ *Sarcina Lutea* as the test germ.

Table 2 below gives the mean values obtained with the three dogs.

TABLE 2

| Amoxycillin | | | FU - 2 | | |
|---|---|---|---|---|---|
| Tube N. | Time | Conc. mcg/ml | Tube N. | Time | Conc. mcg/ml |
| 1 | 30 min. | 4.3 | 1 | 30 min. | 6.3 |
| 2 | 1 hour | 5.3 | 2 | 1 h 5 | 7.8 |
| 3 | 2 hours | 8.1 | 3 | 2 h 5 | 7.8 |
| 4 | 2 h 32 | 9.6 | 4 | 2 h 30 | 9.0 |
| 5 | 3 h 5 | 5.8 | 5 | 3 h 2 | 6.7 |
| 6 | | | 6 | 3 h 5 | 6.0 |
| 7 | 3 h 10 | 4.8 | 7 | 3 h 11 | 6.3 |
| 8 | 3 h 20 | 4.8 | 8 | 3 h 20 | 5.8 |
| 9 | 3 h 30 | 3.9 | 9 | 3 h 30 | 4.6 |
| 10 | 3 h 45 | 3.2 | 10 | 3 h 45 | 4.1 |
| 11 | 4 h | 2.9 | 11 | 4 h | 3.5 |
| 12 | 4 h 15 | 3.0 | 12 | 4 h 15 | 3.0 |
| 13 | 4 h 30 | 2.0 | 13 | 4 h 30 | 3.2 |
| 14 | 5 h | 1.8 | 14 | 5 h | 2.7 |
| 15 | 5 h 14 | 1.3 | 15 | 5 h 20 | 2.7 |
| 16 | 5 h 20 | 1.2 | 16 | 5 h 40 | 3.0 |
| 17 | 5 h 40 | 0.7 | 17 | 6 h | 2.7 |
| 18 | 6 h | 0.78 | 18 | 6 h 30 | 2.2 |
| 19 | 6 h 30 | 0.64 | 19 | 7 h | 3.7 |

Measurements were also made of the maximum concentration attained immediately after injecting rats intravenously with 10 mg of Ampicillin, and with equivalent doses of Amoxycillin and FU-2, together with the average life of the three drugs after this injection.

The values determined are given in Table 3 below.

TABLE 3

| Conc. at time zero | Ampi. 193 mcg/ml | Amoxy. 181 mcg/ml | FU-2 273 mcg/ml |
|---|---|---|---|
| Average life T ½ | 45 min. | 60 min. | 155 min. | b—Oral administration

The tests were carried out on female rats of Wistar stock having a weight of 200-250 g, by administering equimolecular doses of Ampicillin, amoxycillin and FU-2, corresponding to 50 mg/kg of Ampicillin.

The antibiotics were administered in an aqueous solution having a pH of approximately 8.

The antibiotic levels in the blood at the various times were determined by the bacteriological disc diffusion method, using the germ *Sarcina Lutea*. The mean values obtained in tests on 20 rats are given in Table 4 below.

TABLE 4

| Max. conc. | Ampi. 4.5 mcg/ml | Amoxy. 8.3 mcg/ml | FU-2 12.8 mcg/ml |
|---|---|---|---|
| Time for attaining max. conc. | 45 min. | 45 min. | 70 min. |

3. Distribution in the organs

Male rats of Wistar stock having a weight of 80-100 g were used for this determination.

The antibiotics were administered to the rats orally in an aqueous solution of pH 7.4, and in a quantity equivalent to 40 mg/kg of Amoxycillin. The organs were withdrawn 60 minutes after administration, and the tissues homogenised. The antibiotic content was determined by the bacteriological method already used in the preceding tests.

The mean values obtained, expressed in mcg of antibiotic per gram of tissue, are given in Table 5 below.

TABLE 5

| | Amoxy. | FU-2 |
|---|---|---|
| lung | 5.1 | 12.6 |
| liver | 14.6 | 14.2 |
| kidney | 12.2 | 21.7 |
| plasma | 14.5 | 16.9 |

From this pharmacological data it can be clearly seen that the plasmatic levels attained with the new compound FU-2 according to the invention are higher and more lasting than those attained by Ampicillin and Amoxycillin.

It was also found that the compound FU-2 is much more specific on the lung and kidney than Amoxycillin, whereas it has approximately the same activity on the liver.

4. Range of Spectrum

The minimum inhibiting concentration of the new compound was determined with respect to a certain number of microorganisms, in comparison with Ampicillin and Amoxycillin.

The values obtained are given in Table 6 below.

TABLE 6

| Microorganism | Amoxycillin mcg/ml | Ampicillin mcg/ml | FU-2 mcg/ml |
|---|---|---|---|
| *Staphylococcus epidermidis* (349) | 0.25 | 0.25 | 0.25 |
| *Staphylococcus aureus* (209) | 0.25 | 0.25 | 0.25 |
| *Escherichia coli* (100) | 4 | 4 | 4 |
| Enterobacter sp (62) | 128 | 128 | 128 |
| Proteus (327) | 2 | 2 | 2 |
| *Escherichia coli* (233) | 128 | 128 | 129 |
| Salmonella (18) | 128 | 128 | 128 |
| *Staphylococcus aureus*(2) | 0.125 | 0.125 | 0.125 |

This orientative screening shows that the new antibiotic FU-2 is active against all the microorganisms generally attacked by penicillins.

5. Toxicity

The new compound is practically free from toxicity, as is shown by the following $DL_{50}$ values.

$DL_{50}$ in the mouse by oral administration: 12.5 g/kg $DL_{50}$ in the mouse by intraperitoneal administration: 5.1 g/kg DL₅₀ in the rat by intraperitoneal administration: 2.8 g/kg

6. Hematic Levels in Man

The results are given below of a series of cross tests carried out on three women patients, by administering FU-2 and Amoxycillin with one days difference between them.

In total, the data was analysed for the following patients:
3 patients with complete FU-2 and Amoxycillin curves
3 patients with complete FU-2 and partial Amoxycillin curves
3 patients only with FU-2 curves.

The patients had an average age of 49 years (18–67) and an average weight of 57 kg (41–86 kg).

Capsules were administered containing 500 mg of antibiotic, but in each case the values obtained were standardised at 20 mg/kg. Blood samples were taken at the times indicated after administering the drug, and were preserved at approximately 5° C. until the moment of analysis.

The analysis was carried out by a microbiological method, titrating the inhibition caused by discs impregnated with the plasma on Agar of *Sarcina Lutea* after 18 hours of incubation at 37° C.

The determined hematic levels expressed in mcg/ml are given in Table 7.

TABLE 7

| Subject | Product | 0.5 | 1.0 | 1.5 | 2.0 | 3.0 | 4.0 | 6.0 | 8.0 |
|---|---|---|---|---|---|---|---|---|---|
| 4 | Amoxy. | 1.9 | 0.2 | 11.9 | 16.4 | 11.9 | 4.8 | 0.4 | 0.3 |
|   | FU-2 | 0.5 | 3.3 | 13.9 | 19.4 | 17.4 | 13.3 | 3.3 | 0.8 |
| 5 | Amoxy. | 17.2 | 1.4 | 10.3 | 29.5 | 15.4 | 9.5 | 2.3 | 0.5 |
|   | FU-2 | 8.2 | 22.3 | 24.6 | 22.3 | 8.2 | 3.8 | 1.3 | 0.7 |
| 6 | Amoxy. | 0 | 0.7 | 15.4 | 19.2 | 17.3 | 8.1 | 1.7 | 0.7 |
|   | FU-2 | 5.4 | 22.8 | 39.4 | 44.2 | 28.3 | 31.7 | 1.8 | 0.7 |
| 4 | Amoxy. | 0.2 | 0.1 | 11.9 | 11.9 | 14.5 | 10.8 |   |   |
|   | FU-2 | 4.3 | 4.3 | 18.9 | 18.9 | 17.2 | 10.0 | 2.2 | 0.7 |
| 5 | Amoxy. | 1.8 | 2.3 | 16.5 | 16.5 |   |   |   |   |
|   | FU-2 | 9.6 | 9.6 | 22.5 | 22.5 | 16.5 | 7.8 | 2.3 | 1.7 |
| 6 | Amoxy. | 0.2 | 0.03 | 10.7 | 10.7 | 7.9 | 7.1 |   |   |
|   | FU-2 | 3.1 | 3.1 | 14.3 | 14.3 | 14.3 | 9.9 | 0.6 | 0.2 |

As can be seen, the human tests confirmed that which had already been seen in the pharmacological tests (as stated, the data given represent only a proportion, illustrative of a large number of tests carried out), i.e. that the new antibiotic attains greater hematic levels and has a more prolonged action than the best known penicillins, and in particular than Amoxycillin.

7. Pharmacokinetic Characteristics in Man 20 mg/kg of Amoxycillin and the equivalent (equimolecular) quantity of FU-2 were administered orally to 7 women patients.

Table 8 below gives some values taken from the determination of the curve of plasmatic concentration against time after administration (the standard deviation is given in parentheses).

TABLE 8

| Parameter | FU-2 | Amoxy. |
|---|---|---|
| (1) C. max. mg/ml | 28.0 (14.3) | 17.8 (5.5) |
| (2) T. max. h | 2.1 (0.4) | 2.1 (0.5) |
| (3) AUC mg.h/ml | 80.2 | 67.5 |

The parameter (1) indicates the maximum concentration of antibiotic attained in the blood, and the parameter (2) the time after administration necessary for attaining maximum concentration. As can be seen, the value of T is equal for the two antibiotics, but within the same time interval the concentration of FU-2 attained is considerably higher.

The AUC (area under curve) is a value proportional to the quantity of product absorbed by the organism. Again in this case the parameter considered clearly indicates superiority of the new compound FU-2. Summarising, the new penicillin according to the invention is a wide spectrum antibiotic which is stable with time even in a humid environment and at elevated temperature, is more active and of more prolonged effect than Ampicillin and Amoxycillin, is more bioavailable and in particular is more specific for the lung and kidney than these latter compounds. Moreover, the new antibiotic is practically free from toxicity.

The product according to the present invention can be administered orally, parenterally, intravenously or rectally, diluted in suitable carriers normally used in pharmaceutical technology.

By way of example, a formulation is given hereinafter for oral administration in capsules.

Each capsule contains:
FU-2: 500 mg
lactose: 80 mg
Mg stearate: 10 mg

In the pharmacological and clinical tests carried out up to the present time, the compound FU-2 has proved particularly useful in treating infections of the oral sphere (angina, rhinopharyngitis, sinusitis, adenoiditis), in broncho-pulmonary infections (acute and chronic bronchitis, broncho-pneumonia, pneumonia, pleuritis), in infections of the urinary tracts (cystitis, nephritis, acute and chronic pyelonephritis, prostatitis), in infections during gynaeological surgery, in infections of the digestive and hepatobiliary system, and in cutaneous infections.

Good results were obtained in all cases by administering one capsule of 500 mg twice per day during light infections, and two capsules twice a day for acute infections.

What we claim is:

1. Furfuryleneamino-p.hydroxybenzyl-penicillin of the formula:

$$\text{HO}-\text{C}_6\text{H}_4-\underset{\underset{\text{CH}}{\overset{\|}{\text{N}}}{\text{CH}}}{\text{CH}}-\text{CO}-\text{NH}-\text{CH}-\text{CH}-\text{S}\cdots\text{C}(\text{CH}_3)_2-\text{CH}(\text{COOR})-\text{N}-\text{CO} \quad (I)$$

in which R=H, Na or K, and its imidazolidone isomer form.

2. A therapeutic composition comprising an antibacterially effective amount of a compound of the formula:

$$\text{HO}-\text{C}_6\text{H}_4-\underset{\underset{\text{CH}}{\overset{\|}{\text{N}}}{\text{CH}}}{\text{CH}}-\text{CO}-\text{NH}-\text{CH}-\text{CH}-\text{S}\cdots\text{C}(\text{CH}_3)_2-\text{CH}(\text{COOR})-\text{N}-\text{CO}$$

in which R=H, Na or K, and a therapeutically acceptable carrier.